(12) United States Patent
Amar et al.

(10) Patent No.: US 8,709,454 B2
(45) Date of Patent: Apr. 29, 2014

(54) COMBINATION OF A MICROORGANISM AND A PHYTOSPHINGOSINE DERIVATIVE, COMPOSITION, METHODS OF USE

(75) Inventors: David Amar, Paris (FR); Bruno Bernard, Courbevoie (FR); Dominique Bernard, Vanves (FR); Isabelle Castiel, Nice (FR)

(73) Assignee: L'Oreal, Paris (FR)

( * ) Notice: Subject to any disclaimer, the term of this patent is extended or adjusted under 35 U.S.C. 154(b) by 245 days.

(21) Appl. No.: 12/685,697

(22) Filed: Jan. 12, 2010

(65) Prior Publication Data

US 2010/0203094 A1 Aug. 12, 2010

(30) Foreign Application Priority Data

Jan. 12, 2009 (FR) .................................... 09 50143

(51) Int. Cl.
| | | |
|---|---|---|
| *A61K 8/06* | (2006.01) | |
| *A61K 8/11* | (2006.01) | |
| *A61K 8/99* | (2006.01) | |
| *A61Q 19/08* | (2006.01) | |

(52) U.S. Cl.
USPC .......... 424/401; 424/93.4; 514/944; 514/937; 514/741; 514/728; 514/720; 514/75; 514/120; 514/129; 514/159; 514/162; 514/579

(58) Field of Classification Search
USPC .......... 514/944, 937, 741, 727, 728, 720, 75, 514/120, 129, 159, 162, 579; 424/401, 93.4
See application file for complete search history.

(56) References Cited

U.S. PATENT DOCUMENTS

| 4,464,362 A | * | 8/1984 | Kludas et al. ................. 424/114 |
| 5,326,565 A | | 7/1994 | Critchley et al. |
| 5,882,665 A | * | 3/1999 | Meyers et al. ................. 424/401 |

FOREIGN PATENT DOCUMENTS

| EP | 0 043 128 | 1/1982 |
| EP | 0 919 226 | 6/1999 |
| EP | 0 919 266 | 6/1999 |
| EP | 1 593 382 | 11/2005 |
| EP | 1 609 463 | 12/2005 |
| EP | 1 642 570 | 4/2006 |
| EP | 1 731 137 | 12/2006 |
| FR | 2 876 029 | 4/2006 |
| FR | 2 905 856 | 3/2008 |
| WO | WO 02/28402 | 4/2002 |
| WO | WO 2006/000992 | 1/2006 |
| WO | WO 2006/037922 | 4/2006 |

OTHER PUBLICATIONS

Paragh, Schling, Ugoscai, Liebisch: "Novel Sphingolipid Derivatives Promote Keratinocyte Differenciation," Experimental Dermatology, vol. 17, No. 12, Mar. 17, 2008 (pp. 1004-1016) XP002543996.

* cited by examiner

*Primary Examiner* — Richard Schnizer
*Assistant Examiner* — Alma Pipic
(74) *Attorney, Agent, or Firm* — Oblon, Spivak, McClelland, Maier & Neustadt, L.L.P.

(57) ABSTRACT

At least one phytosphingosine salicylate derivative and at least one lysate of at least one microorganism of the genus *Bifidobacterium*. Composition, combination. Use, including cosmetic use for reinforcing the repair and regeneration capacity of an epithelium, especially an epidermis, in particular an aged epidermis.

8 Claims, 1 Drawing Sheet

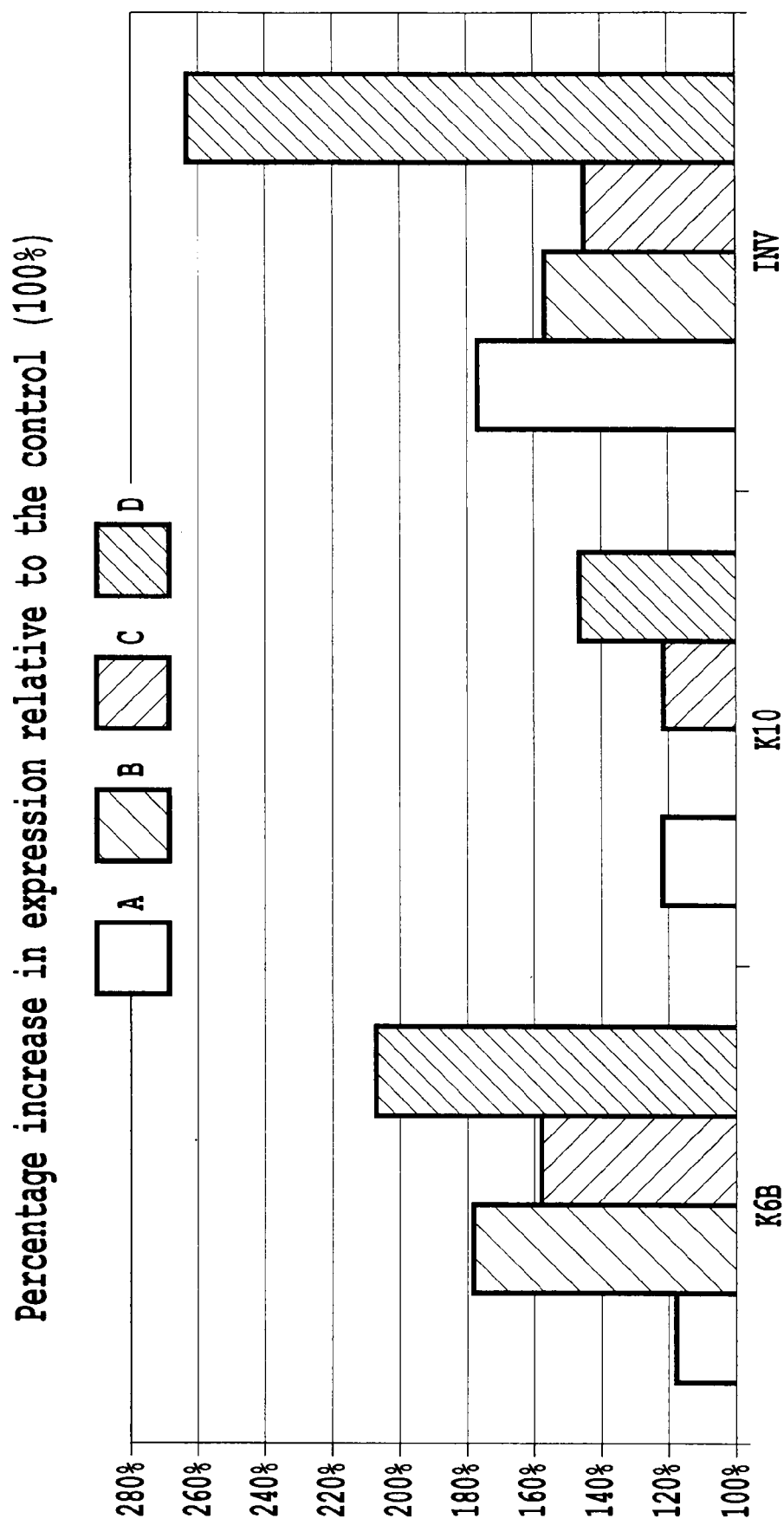

COMBINATION OF A MICROORGANISM AND A PHYTOSPHINGOSINE DERIVATIVE, COMPOSITION, METHODS OF USE

REFERENCE TO PRIOR APPLICATIONS

This application claims priority to U.S. provisional application Ser. No. 61/146,319, filed Jan. 22, 2009; and to French patent application 09 50143, filed Jan. 12, 2009, both incorporated herein by reference.

FIELD OF THE INVENTION

The present invention provides a particularly advantageous composition comprising, and a particularly advantageous combination of, a lysate of a microorganism and a phytosphingosine derivative, the compositions and combinations being useful, for example, for preventing, preventing the appearance of, and/or treating skin aging. In the description herein, where a composition is described, a combination is included, and vice versa.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

The epidermis is an epithelium, conventionally divided up into a basal layer of keratinocytes containing, in particular, skin stem cells and constituting the germinative layer of the epidermis, a "spiny" layer constituted of several layers of polyhedral cells placed on the basal layer, a "granular" layer comprising one to three layers said to be of flattened cells containing distinct cytoplasmic inclusions, keratohyalin granules, and finally, a set of upper layers, called horny layer (or stratum corneum) constituted of keratinocytes at the terminal stage of their differentiation, called corneocytes.

The stratum corneum, or horny layer, is the superficial layer of the epidermis located at the interface between the organism and its environment. It is composed of corneocytes, which are anucleate cells resulting from the differentiation of epidermal keratinocytes. The corneocytes are rich in keratins and are surrounded by an impermeable lipid matrix. By virtue of its protein and lipid composition, the stratum corneum plays an essential skin barrier role. It prevents the intrusion of microbiological agents and makes it possible to preserve the hydration of the skin and therefore of the body in general.

During skin aging, and other than the well-known consequences of age on the relief of the skin, many forms of discomfort are reported by elderly individuals. These forms of discomfort are caused by an impairment of the barrier function and of the epidermal homeostasis of their skin. Thus, the stratum corneum of aged skin has a reduced intercellular lipid content compared with young skin, particularly during the winter period. This change in composition of the stratum corneum disrupts its physicochemical skin barrier properties. Finally, the speed of recovery of the barrier function after impairment of the stratum corneum slows down with age, implying a dysfunction of the homeostatic function of the epidermis (Denda, M., 2002; Ghadially, R. et al, 1995; Leveque, J. L., 2001). The Applicant company has, in addition, observed, under these same circumstances, that, in response to a physical or chemical attack on the stratum corneum, particular genes show modulation kinetics that are significantly different according to the age of the individual. More specifically, the induction of the expression of certain genes is found to be slowed in aged skin, in comparison with young skin.

Among these genes of which the expression is particularly slowed in elderly individuals exposed to a stress is in particular the keratin 6B gene (KRT6B) which has, moreover, been characterized as particularly advantageous from the viewpoint of its involvement in epidermal repair and regeneration processes.

Moreover, the homeostasis of the skin, and in particular of the epidermis, results from a finely regulated balance between the processes of proliferation and differentiation of the cells of the skin. These proliferation and differentiation processes are perfectly regulated: they participate in the renewal and/or regeneration of the skin and lead to the maintenance of a constant skin thickness, and in particular a constant epidermal thickness. This homeostasis of the skin is also involved in maintaining the mechanical properties of the skin.

However, this homeostasis of the skin can be impaired by certain physiological factors (age, menopause, hormones, etc.) or environmental factors (UV stress, pollution, oxidative stress, irritant stress, etc.). The regenerative potential of the epidermis becomes less great: the cells of the basal layer divide less actively, which leads in particular to a slowing down and/or a decrease in epidermal renewal. Consequently, cell renewal no longer compensates for the loss of the cells removed at the surface, leading to atrophy of the epidermis and/or to a decrease in the thickness of the skin and/or a loss of elasticity and/or of firmness of the skin.

The alterations in epidermal homeostasis are also reflected by a dull and/or poorly defined appearance to the complexion of the skin.

This phenomenon may be accentuated by the menopause: women complain of their skin tightening and becoming dry, or even of the appearance of xerosis. The hormonal deficits associated with the menopause are accompanied in particular by a drop in metabolic activity, which could result in a decrease in the proliferation of the keratinocytes and an increase in epidermal differentiation.

It is therefore advantageous to also have available compositions capable of promoting the homeostasis of the skin in order to maintain and/or increase the thickness of the skin and thus to maintain and/or improve the mechanical properties of the skin and/or promote the radiance of the complexion.

BRIEF DESCRIPTION OF THE DRAWINGS

FIG. 1 shows the expression kinetics of three studies, described in detail below.

DETAILED DESCRIPTION OF THE PREFERRED EMBODIMENTS

The present invention in its preferred embodiments relates more particularly to the discovery, by the inventors, that certain combinations are effective in meeting the requirements noted above, including promoting the homeostasis of the skin in order to maintain and/or increase the thickness of the skin and thus to maintain and/or improve the mechanical properties of the skin and/or promote the radiance of the complexion, and in particular via a stimulatory action on the expression of certain genes. Furthermore, certain combinations make it possible to compensate for the slowing down of the expression of certain genes, in particular observed during skin aging, as for KRT6B.

Consequently, according to one of its preferred aspects, the present invention relates to a composition that can be used for the care of and/or making up keratin materials, comprising, in a physiologically acceptable medium, at least one phytosphingosine salicylate derivative and at least one lysate of at least one microorganism of the genus Bifidobacterium species (genus Bifidobacterium).

According to another of its preferred aspects, it also relates to a combination comprising at least one lysate of at least one microorganism of the genus Bifidobacterium and at least one phytosphingosine salicylate derivative.

According to another of its preferred aspects, it also relates to the use, in particular cosmetic use, of a combination or composition comprising at least one lysate of at least one microorganism of the genus Bifidobacterium and at least one phytosphingosine salicylate derivative, for stimulating the expression of at least one gene chosen from the KRT6B or KRT10 and involucrin genes.

According to another of its preferred aspects, the present invention relates in a preferred embodiment to the use, including the cosmetic use, of a combination or composition comprising at least one lysate of at least one microorganism of the genus Bifidobacterium and at least one phytosphingosine salicylate derivative, for stimulating the expression of at least one gene chosen from the KRTB6, KRT10 and involucrin genes, to an individual subject to skin ageing.

The combination according to the invention is particularly advantageous for preventing, treating, and/or compensating for the decrease in expression observed with age for the KRT6B gene.

The use of a lysate of microorganisms of the genus Bifidobacterium, such as the Repair Complex CLR lysate, is admittedly known from EP 0 043 128, but only for the purposes of skin cell DNA repair.

For their part, the following documents propose the use of microorganisms, in particular probiotic microorganisms, essentially for the purposes of treating dry and/or sensitive skin and associated conditions, but in a form distinct from a lysate.

Thus, document WO 02/28402 indicates that probiotic microorganisms can have a beneficial effect in the regulation of skin hypersensitivity reactions such as inflammatory and allergic reactions which are the result of an immunological process. Documents EP 1 609 463, EP 1 642 570, EP 1 731 137 and FR2 876 029 describe compositions combining one or more probiotic microorganism(s) with an inorganic cation for the treatment of sensitive skin. As for document PCT/FR2006/050768, it proposes, for the treatment of sensitive skin associated with dry skin, a combination of a probiotic microorganism with a polyunsaturated fatty acid and/or polyunsaturated fatty acid ester. Consequently, none of these documents describes the use of a lysate of a microorganism of the genus Bifidobacterium, and even less in the combined form under consideration according to the invention.

With regard to phytosphingosine and salts thereof, and more particularly the hydrochloride thereof, they have already been proposed in the dermatology field. In fact, phytosphingosine is first of all known for its antimicrobial activity. Thus, phytosphingosine is already used to advantage, in terms of this activity, in the treatment of acne and in terms of its inhibitory activity on the growth of microorganisms on the skin (U.S. Pat. No. 5,326,565 and EP 0 919 226). More recently, sphingolipid derivatives, and in particular derivatives of phytosphingosine salicylate type, have been described as showing an ability to modulate keratinocyte differentiation (G Paragh et al; *Exp Dermatol.* 2008 December; 17(12):1004-16). Document U.S. Pat. No. 5,882,665, for its part, proposes novel phytosphingosine salicylate derivatives described as being of use as anti-acne agents, antibacterial agents, antiwrinkle agents, and also skin-lightening agents.

However, to the inventors' knowledge, the beneficial or even synergistic effect shown by a combination of a phytosphingosine salicylate derivative and of a lysate of a microorganism of the genus Bifidobacterium, on the expression of certain genes, has never been noted.

As used herein the term "synergistic" and its derivatives means a greater than additive effect.

As shown by the examples hereinafter, a combination in accordance with the invention clearly stimulates the expression of the KRT6B gene, but also of the KRT10 and involucrin genes. This action has in particular been verified by qRT-PCR using an Episkin® reconstructed skin model.

For the purpose of the invention, the effect shown by the combination is defined as synergistic since it proves to be greater than that expected from the simple superimposition of the respective effects of the phytosphingosine salicylate derivative and of the lysate of a microorganism of the genus Bifidobacterium. Such combinations are synergistic combinations.

According to another of its aspects, the present invention relates to the use of the compositions and combinations considered above, for reinforcing the repair and regeneration capacity of an epithelium, especially of an epidermis, in particular an aged epidermis.

According to another of its aspect, the present invention relates to the use of at least one lysate of at least one microorganism of the genus Bifidobacterium in combination with at least one phytosphingosine salicylate derivative, for the preparation of a composition for reinforcing the repair and regeneration capacity of an epithelium, especially an epidermis, in particular an aged epidermis.

As emerges from the above, this effect is in particular obtained via stimulation of the expression of a gene or genes naturally slowed during the skin aging process, and more particularly via stimulation of the expression of KRT6B.

According to one of its aspect, the present invention relates to the use, namely cosmetic use of a combination comprising at least one lysate of at least one microorganism of the genus Bifidobacterium and at least one phytosphingosine salicylate derivative, for stimulating the expression of at least one gene chosen from the KRTB6, KRT10 and involucrin genes for reinforcing the repair and regeneration capacity of an epithelium, especially of an epidermis, in particular an aged epidermis.

According to yet another of its aspects, the present invention relates to a method of treatment, in particular cosmetic treatment, comprising at least the administration, to an individual subject to skin aging, of the combination considered above.

This administration may be carried out in particular orally or topically.

The invention also relates to the cosmetic use, in particular in a composition containing a physiologically acceptable medium and devoted to topical application to the skin, of a combination according to the invention, for increasing the thickness of the skin, promoting the radiance of the complexion, promoting and/or improving the mechanical properties of the skin, and/or promoting and/or improving the elasticity and/or the firmness of the skin.

Microorganisms of the Genus *Bifidobacterium*

As specified above, the microorganisms of the genus *Bifidobacterium* employed as active agents according to the invention are used in the form of a lysate.

A lysate commonly denotes a material obtained at the end of the destruction or dissolution of biological cells by means of a phenomenon termed cell lysis, thus causing release of the intracellular biological constituents naturally contained in the cells of the microorganism under consideration.

For the purpose of the present invention, the term "lysate" is used without distinction to denote the entire lysate obtained by lysis of the microorganism concerned, or only a fraction thereof.

Thus, the invention relates to the use of a lysate of *Bifidobacterium* species and/or a fraction thereof.

The lysate used is therefore entirely or partly formed from the intracellular biological constituents and from the constituents of the cell walls and membranes.

More specifically, it contains the cytoplasmic cell fraction containing the enzymes such as lactic acid dehydrogenase, phosphatases, phosphoketolases and transaldolases, and the metabolites. By way of illustration, the cell wall constituents are in particular peptidoglycan, murein or mucopeptide and teichoic acid, and the cell membrane constituents are composed of glycerophospholipid.

This cell lysis may be accomplished by means of various technologies, such as, for example, osmotic shock, heat shock, by ultrasound, or else under mechanical stress of the centrifugation type.

More particularly, this lysate can be obtained according to the technology described in U.S. Pat. No. 4,464,362, and in particular according to the following protocol.

A microorganism of *Bifidobacterium* type under consideration is cultured anaerobically in a suitable culture medium, for example according to the conditions described in documents U.S. Pat. No. 4,464,362 and EP 0 043 128. When the stationary phase of development has been reached, the culture medium can be inactivated by pasteurization, for example at a temperature of from 60 to 65° C. for 30 min. The microorganisms are then recovered by means of a conventional separation technique, for example membrane filtration, centrifuged, and resuspended in a sterile solution of NaCl at a physiological concentration. The lysate can be obtained by disintegration of such a medium with ultrasound, in order to release therefrom the cytoplasmic fractions, the cell wall fragments and the metabolism-derived products. Next, all the components in their natural distribution are subsequently stabilized in a weakly acidic aqueous solution.

A lysate having a concentration of the order of from 0.1% to 50%, in particular from 1% to 20%, and especially approximately 5% by weight of active material(s), relative to the total weight thereof, is thus generally obtained.

The lysate may be used in various forms, in the form of a solution or in pulverulent form.

A microorganism most particularly suitable for the invention, belongs to the genus *Bifidobacterium* and is preferably chosen from the species: *Bifidobacterium longum, Bifidobacterium bifidum, Bifidobacterium breve, Bifidobacterium animalis, Bifidobacterium lactis, Bifidobacterium infantis, Bifidobacterium adolescentis* or *Bifidobacterium pseudocatenulatum*, and mixtures thereof.

The species *Bifidobacterium longum* is most particularly suitable for the invention.

The lysate may advantageously be the lysate registered under the INCI name: Bifidat ferment Lysate, under the EINECS name: *Bifidobacterium longum*, under EINECS No.: 306-168-4 and under CAS No.: 96507-89-0.

The product sold under the name Repair Complex CLR® by the company K. Richter GmbH and which is formed from an inactivated lysate of the species *Bifidobacterium longum*, falls within the context of the invention.

A lysate useful according to the present invention is such as defined above.

Phytosphingosine Salicylate Derivative

Naturally, phytosphingosine, which is present in the stratum corneum, corresponds to one of the three sphingoid bases naturally present in the skin.

In the context of the present invention, the phytosphingosine derivatives more particularly considered are the derivatives of phytosphingosine salicylate type, i.e. compounds derived from the covalent bonding of at least one phytosphingosine molecule to at least one salicyclic acid molecule. This bonding may be of ester or amide type, and preferably is of amide type.

For the purpose of the invention, these phytosphingosine salicylate derivatives include the various ionic forms of the corresponding compounds.

Such a derivative advantageously corresponds to the following structural formula:

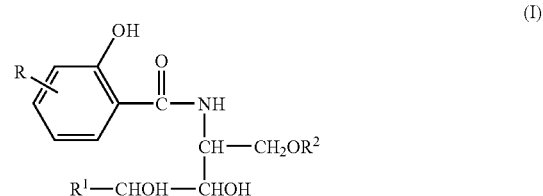

(I)

in which:

R represents:

a hydrogen atom, a saturated or unsaturated, linear or branched $C_1$ to $C_{49}$ aliphatic radical, where appropriate substituted with a hydroxyl radical, or a group $Y-O(C_aH_b)_m-$, with a being an integer from 7 to 50, b an integer from 10 to 100, m is 0 or 1 and Y represents H or a $C_{14}$-$C_{22}$ fatty acid having the following formula: $-CO-(C_xH_yZ_z)CH_3$, with Z being —OH or an epoxy oxygen, x an integer from 12 to 20, y an integer from 20 to 40, and z is 0 or an integer from 1 to 4;

$R^1$ represents a saturated or unsaturated, linear or branched $C_8$ to $C_{28}$, in particular $C_{10}$ to $C_{20}$, especially $C_{12}$ to $C_{18}$, aliphatic radical, where appropriate substituted with a hydroxyl radical; and $R^2$ represents H, a phosphate radical, a sulphate radical or a sugar.

Such derivatives are more particularly described in document EP 919 226.

The derivative of formula I in which R and $R^2$ represent, respectively, a hydrogen atom and $R^1$ a linear and saturated, in particular $C_{14}$, alkyl radical is most particularly suitable for the invention.

This derivative corresponds to the following formula:

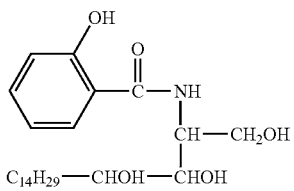

(V)

Such a derivative is in particular sold by the company Evonick Goldschmidt under the name Phytosphingosine SLC.

A phytosphingosine salicylate derivative useful according to the present invention is such as defined above.

The respective amounts of phytosphingosine salicylate derivative and of lysate forming the combination according to the invention, which may be used, also termed "effective amounts", are not limited and depend, of course, on the desired effect and can therefore vary to a large extent.

For the purpose of the present invention, the expression "effective amount" is intended to denote the minimum amount necessary in order to observe the expected effect, namely a cosmetic effect or a therapeutic effect, it being understood that the effective amounts necessary for obtaining a cosmetic effect or a therapeutic effect may, as appropriate, be identical or different.

To give an order of magnitude, each of the two compounds forming the invention may be present in an amount representing from 0.0001% to 50% and more of the total weight of the composition, in particular in an amount representing from 0.001% to 10% of the total weight of the composition.

More particularly, in the composition according to the present invention, the active agent forming the lysate and belonging to the genus *Bifidobacterium* may be used in a proportion of at least 0.001% (expressed as dry weight), in particular in a proportion of from 0.01% to 20%, and more particularly in a proportion of from 0.01% to 15% by dry weight of active material, relative to the total weight of the support or of the composition containing same.

The phytosphingosine salicylate derivative, for its part, in the composition according to the present invention may be formulated in a composition in a proportion of from at least 0.0001% (expressed as dry weight), in particular in a proportion of from 0.001% to 20%, and more particularly in a proportion of from 0.05% to 2% by dry weight of active material, relative to the total weight of the support or of the composition containing same.

Composition and Combination According to the Invention

The compositions and combinations under consideration according to the invention may be suitable for cosmetic and/or pharmaceutical, in particular for dermatological use.

For the purpose of the invention, the expression "prevention of a condition" is intended to mean the slowing of the occurrence of conditions associated with skin aging, in particular as defined above. The "treatment of a condition" is another term that can be used, e.g., to mean the slowing of the occurrence of conditions associated with skin aging, or the slowing of appearance of conditions associated with skin aging.

It is preferred that all the compositions and combinations under consideration according to the invention use a physiologically acceptable medium.

For the purpose of the present invention, the term "physiologically acceptable medium" is intended to denote a medium that is suitable for the application of a composition and a combination to a keratin material, in particular the skin.

According to one particular embodiment, a composition and a combination in accordance with the invention may also comprise at least one supplementary agent that is active on the skin.

The amounts of the various constituents that can supplement the composition and combination according to the invention include those conventionally used in the fields under consideration.

Supplementary Active Agents

As examples of supplementary active agents that can be used in the context of the present invention, mention may be made of active agents for improving the condition of the skin, such as hydrating or moisturizing active agents, or active agents for improving the natural lipid barrier, such as ceramides, cholesterol sulphates and/or fatty acids, and mixtures thereof.

It may also be possible to use enzymes which have an activity on the skin, such as proteases, lipases, cerebrosidases, amidases and/or melanases, and mixtures thereof.

It is also possible to use active agents of the microorganism, in particular probiotic microorganism, type, such as those described in applications WO 2006/000992 and WO 2006/037922.

For the purpose of the present invention, the term "probiotic microorganism" is intended to mean a live microorganism which, when it is consumed in suitable amount, has a positive effect on the health of its host according to the "Joint FAO/WHO Expert Consultation on Evaluation of Health and Nutritional Properties of Probiotic in Food Including Powder Milk with Live Lactic Acid Bacteria, 6 Oct. 2001", and which may in particular improve the intestinal microbial balance.

The microorganisms suitable for the invention may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, and mixtures thereof.

As ascomycetes most particularly suitable for the present invention, mention may in particular be made of *Yarrowia lipolitica* and *Kluyveromyces lactis*, and equally *Saccharomyces cereviseae, Torulaspora, Schizosaccharamyces pombe, Candida* and *Pichia*.

Specific examples of probiotic microorganisms are *Bifidobacterium bifidum, Bifidobacterium infantis, Lactobacillus acidophilus, Lactobacillus alimentarius, Lactobacillus curvatus, Lactobacillus delbruckii* subsp. *Lactis, Lactobacillus gasseri, Lactobacillus johnsonii, Lactobacillus reuteri, Lactobacillus rhamnosus (Lactobacillus GG), Lactobacillus sake, Lactococcus lactis, Streptococcus thermophilus, Staphylococccus carnosus* and *Staphylococcus xylosus*, and mixtures thereof.

More particularly, they are probiotic microorganisms derived from the group of lactic acid bacteria, such as in particular *Lactobacillus* and/or *Bifidobacterium*. By way of illustration of these lactic acid bacteria, mention may more particularly be made of *Lactobacillus johnsonii, Lactobacillus reuteri, Lactobacillus rhamnosus, Bifidobacterium bifidum, Bifidobacterium breve, Bifidobacterium animalis, Bifidobacterium lactis, Bifidobacterium longum,*

*Bifidobacterium infantis*, *Bifidobacterium adolescentis* or *Bifidobacterium pseudocatenulatum*, and mixtures thereof.

A strain of *Bifidobacterium lactis* may be obtained from Hansen (Chr. Hansen A/S, 10-12 Boege Alle, P.O. Box 407, DK-2970 Hoersholm, Denmark) under the name Bb 12.

The microorganism(s) may be included in the composition according to the invention in a live, semi-active or inactivated, dead form.

It (they) may also be included in the form of cell component fractions or in the form of metabolites. The microorganism(s), metabolite(s) or fraction(s) may also be introduced in the form of a lyophilized powder, of a culture supernatant and/or, as appropriate, in a concentrated form.

In the particular case of the topical compositions, it may be advantageous to use these microorganisms in inactivated, or even dead form.

With regard to the probiotic microorganisms, the following bacterial and yeast genera are generally used:

Lactic acid bacteria: which produce sugar from lactic acid, by fermentation. They are divided up into two groups according to their morphologies:

*Lactobacillus* species: *acidophilus* (LC1, NCFB 1748); *amylovorus, casei* (Shirota), *rhamnosus* (strain GG), *brevis, crispatus, delbrueckii* (subsp *bulgaricus, lactis*), *fermemtum, helveticus, gallinarum, gasseri, lohnsonii, paracasei, plantarum, reuteri, rhamnosus, salivarius*), Gocci: *Enterocossus (faecalis, faeciul), Lactococcus lactis* (subspp *lactis* or *cremoris*), *Leuconstoc mesenteroides* subsp *dextranicum, Pediococcus acidilactici* (animal feed), *Sporolactobacillus inulinus, Streptococcus salvarius* subsp. *Thermophilus*, Bifidobacteria or bifidobacterium species: *Bifidobacterium adolescentis; animalis, bifidum, breve, lactis, longum, infantis*, Yeasts: *Saccharomyces (cerevisiae* or *boulardii*), The other sporulated bacteria: *Bacillus (cereus var toyo* or *subtilis), Bacillus coagulans, B. licheniformis, Escherichia coli* strain nissle, *Propionibacterium freudenreichii*.

Lactic acid bacteria and bifidobacteria are the probiotics most commonly used.

Specific examples of probiotic microorganisms most particularly suitable for the invention are *Bifidobacterium bifidum, Bifidobacterium infantis, Bifidobacterium longum, Lactobacillus acidophilus, Lactobacillus alimentarius, Lactobacillus casei* subsp. *Casei, Lactobacillus casei Shirota, Lactobacillus paracasei, Lactobacillus curvatus, Lactobacillus delbruckii* subsp. *Lactis, Lactobacillus gasseri, Lactobacillus johnsonii, Lactobacillus reuteri, Lactobacillus rhamnosus (Lactobacillus GG), Lactobacillus sake, Lactococcus lactis, Streptococcus thermophilus, Staphylococccus carnosus* and *Staphylococcus xylosus*, and mixtures thereof.

More particularly, they are probiotic microorganisms derived from the group of lactic acid bacteria, such as in particular *Lactobacillus* and/or *Bifidobacterium*. By way of illustration of these lactic acid bacteria, mention may more particularly be made of *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis* or *Bifidobacterium pseudocatenulatum*, and mixtures thereof.

The species most particularly suitable are *Lactobacillus johnsonii, Lactobacillus paracasei, Bifidobacterium adolescentis, Bifidobacterium longum* and *Bifidobacterium Lactis* NCC 2818 (also denoted Bb12 ATCC 27536) respectively deposited according to the treaty of Budapest with the Institut Pasteur (28 rue du Docteur Roux, F-75024 Paris cedex 15) on 30 Jun. 1992, 12 Jan. 1999, 15 Apr. 1999, 15 Apr. 1999 and 6 Jun. 2005 under the following references CNCM I-1225, CNCM I-2116, CNCM I-2168 and CNCM I-2170 and CNCM I-3446, and the genus *Bifidobacterium longum* (BB536). The *Bifidobacterium lactis* strain CNCM I-3446 can be obtained from Hansen (Chr. Hansen A/S, 10-12 Boege Alle, P.O. Box 407, DK-2970 Hoersholm, Denmark).

Other examples of active agents suitable for the use of the present invention include: analgesic active agents, anti-yeast active agents, antibacterial active agents, antiparasitic active agents, antifungal active agents, antiviral active agents, steroidal anti-inflammatory active agents, anaesthetic active agents, antipruritic active agents, keratolytic active agents, free-radical-scavenging active agents, antiseborrhoeic active agents, antidandruff active agents, anti-acne active agents, active agents aimed at preventing skin aging and/or at improving the condition of the skin, anti-aging active agents, antidermatitis active agents, anti-irritant active agents, immunomodulatory active agents, active agents for treating dry skin, antiperspirant active agents, antpsoriatic active agents, antihistamine active agents, healing active agents, self-tanning active agents, antioxidants such as green tea or active fractions thereof, glycerol, laponite, caffeine, aromatic essential oils, depigmenting active agents, exfoliant active agents, liporegulators, softening, refreshing, deodorizing, desensitizing, bleaching or nourishing active agents, and active agents for reducing cutaneous differentiation and/or proliferation and/or pigmentation, and mixtures thereof.

The supplementary active agents may also be chosen from agents for improving barrier function, dermodecontracting agents, anti-glycation agents, agents for stimulating the synthesis of dermal and/or epidermal macromolecules and/or for preventing their degradation, agents for stimulating fibroblast or keratinocyte proliferation and/or keratinocyte differentation, agents for promoting maturation of the horny envelope, NO-synthase inhibitors, peripheral benzodiazepine receptor (PBR) antagonists, agents for increasing the activity of the sebaceous gland, agents for stimulating the energy metabolism of cells, tensioning agents, fat-restructuring agents, slimming agents, agents for promoting cutaneous capillary circulation, calmatives, sebum-regulating or antiseborrhoeic agents, astringents, anti-inflammatories and anti-acne agents.

Among the active agents and in particular the anti-aging active agents that may be used in the context of the present invention, mention may be made, by way of nonlimiting examples, of: extracts of soya bean proteins, such as the product sold by the company Silab under the trade name Raffermine®, adenosine or synthetic adenosine such as the product sold by Pharma Waldoff, pro-xylane, rye seed extracts such as those sold by Silab under the name Coheliss, extracts of alfalfa (luzerne) such as those sold by Silab under the name Vitanol, the tetrapeptide such as the product sold by Cognis under the reference Dermican LS 9745, rice tripeptides and dipeptides such as those available from the company Silab under the reference Nutriskin, *Vigna aconitifolia* seed extracts such as those sold by the company Cognis under the references Vitoptine LS 9529 and Vit-A-Like LS9737, extracts of *Euglena gracilis* such as those available from Sederma under the reference Chronodyn, wheat amino acids coupled to palmitic acid, sold under the reference Deepline PVB (Lipacide PVB) by Seppic, blueberry extracts such as Herbasol Myrtille Extract from the company Cosmetochem, ginger root extracts, aqueous extracts of Shiitake (*Lentinus edodes*) such as Fermiskin from Silab, and antarcticine sold by Lipotec, extracts of *Punica granatum*, argireline SC36 (hexapeptide) from the company Lipotec from the company Lipotec, an extract of oats, such as the product sold by Silab under the reference Reductine, a purple rice extract such as the purple rice extract from the company Oryza, vine flower cell dispersions such as the Fiber Booster *Sequoia vitis* flower from the company Naolys, ferullic acid, such as Oryzaferulix from the company Oryza Oil and Fat, extracts of *Voandzeia subterranea* (Bambara), such as Filadyn LS 9397 from the company Cognis, soya bean extracts, such as the product Elhibin sold by the company Pentapharm, a hydrolysed *Prunus domestica* fruit extract, such as the reference Clairju from the company Ichimaru Pharco.

In particular, among the other agents that are active on the skin and suitable for the invention, mention may be made of hydrating and/or desquamating active agents such as glycol, urea or its derivatives, HEPES, chelating agents, detergents and jasmonic acid derivatives, and mixtures thereof.

Those skilled in the art will select said active agent(s) according to the desired effect on the keratin materials.

Galenical Forms

For oral administration, a composition of the invention may be in any of the suitable forms, particularly in the form of an oral solution, a syrup, a tablet, a sugar-coated tablet, a gel capsule, a capsule or else a nutritional food or a nutritional supplement.

A composition according to the invention may also comprise at least one appropriate excipient suitable for oral administration.

The combination under consideration according to the invention, in the same way as any composition containing it, may advantageously be administered topically.

A composition devoted to topical administration may in particular be in the form of an aqueous, aqueous-alcoholic or oily solution, a dispersion of the solution type or dispersion of the lotion or serum type, an emulsion with a liquid or semi-liquid consistency of the milk type, obtained by dispersion of a fatty phase in an aqueous phase (O/W) or vice-versa (W/O), or a suspension or emulsion of soft, semi-solid or solid consistency of the cream type, an aqueous or anhydrous gel, or else a microemulsion, microcapsules, microparticles, or vesicular dispersions of ionic and/or nonionic type.

The pH of a composition according to the invention, when it comprises at least one aqueous phase (for example: aqueous solutions, emulsions, etc.), is preferably between 4 and 9, preferably between 4 and 7, advantageously from 5 to 6, and in particular a pH of 5.5.

The composition according to the invention may be more or less fluid and have the appearance of a white or coloured cream, an ointment, a milk, a lotion, a serum, a paste or a foam. It may optionally be applied to the skin in the form of an aerosol. It may also be in solid form, and for example in the form of a stick. It may be used as a care product, but also as a toiletry product and/or a makeup product.

This composition may constitute a mask, a cleansing, protection, treatment or care cream for the face, for the hands, for the feet or for the body (for example, day creams, night creams, makeup-removing creams, foundation creams, anti-sun creams), a makeup-removing milk, or a skin care lotion, gel or foam, such as a cleansing lotion.

In general, any composition of the invention may be applied to the skin (on any area of the skin of the body) or to the mucous membranes (oral, jugal, gingival, genital, conjunctival, etc.).

In a known manner, a cosmetic composition may also contain adjuvants that are customary in the cosmetics field, such as hydrophilic or lipophilic gelling agents, hydrophilic or lipophilic additives, preservatives, antioxidants, solvents, fragrances, fillers, UV (sun) screens, odour absorbers and dyestuffs. The content and the nature of the ingredients used in the compositions of the invention are adjusted by those skilled in the art so as not to substantially affect the effect of the combination under consideration according to the invention.

A combination according to the invention may prove to be particularly advantageous for improving moisturization, homeostasis of the skin, and in particular of the epidermis, the skin barrier function, preventing and/or treating epidermal signs of aging, for instance wrinkles, fine lines, loss of firmness, of elasticity, of density and/or of tonicity of an epidermis.

The skin conditions more particularly targeted by the present invention may therefore be dry skin and very dry skin, and in individuals whose skin has an aged appearance, in particular in women who are over the age of 45 and/or post-menopausal, or even very elderly women.

As specified above, the present invention also relates to a method, in particular a cosmetic method, comprising at least the administration, to an individual subject to skin aging, of at least one combination according to the invention.

Such a treatment method may be carried out in particular by topical or oral administration, for example daily, of the combination under consideration according to the invention.

A method according to the invention may comprise a single administration. According to another embodiment, the administration is repeated, for example, 2 to 3 times daily over one day or more, and generally over a sustained period of at least 4 weeks, or even 4 to 15 weeks, with, as appropriate, one or more periods of interruption.

In the description and in the following examples, unless otherwise indicated, the percentages are percentages by weight and the ranges of values worded in the form "between . . . and . . . " include the lower and upper limits specified.

The example and the FIGURE hereinafter are given by way of nonlimiting illustration of the field of the invention.

Example 1

In this example, the lysate used is the product sold under the name Repair Complex CLR® by the company K. RICHTER GmbH and which is formed from an inactivated lysate of the species *Bifidobacterium longum*, and the phytosphingosine salicylate derivative is the product sold by the company Evonick Goldschmidt under the name Phytosphingosine SLC.

The effects of the following four compositions were tested on the differentiation of Episkin® reconstructed epidermis.
  A: formulation support (ethyl alcohol (3%) and water (97%)),
  B: lysate (ethyl alcohol (3%), water (87%), lysate (10%)),
  C: phytosphingosine salicylate (ethyl alcohol (3%), water (96.998%), phytosphingosine salicylate (0.002%)), and
  D: combination in accordance with the invention=(0.002% phytosphingosine salicylate+10% lysate+ethyl alcohol (3%)+water (86.998%)).

J6 Episkin® reconstructed epidermis were placed in 12-well plates containing 2 ml of a maintenance medium and cultured at 37° C. and 5% $CO_2$ for 24 hours. After incubation, the epidermis were treated topically with the test compositions (50 µl/reconstructed epidermis) and incubated for 6 hours.

These effects were characterized by analysing the expression of the cytokeratin 6B (K6B), cytokeratin 10 (K10) and involucrin (INV) genes using a real-time PCR method (quantitative PCR, qPCR) 6 hours after treatment.

1—Protocols Retained a) Analysis of Differential Expression

The expression of the markers selected was evaluated by RT-qPCR on the messenger RNA extracted from the Episkin® reconstructed epidermis of each treatment (the duplicates were pooled before RNA extraction) 6, 24 and 48 hours after treatment.

b) Reverse Transcription

Total RNA extracted from each sample using tri-reagent.

Potentially contaminating DNA traces removed by treatment with the DNA-free system (Ambion ref. 1906). RNA quantified using Nanovue (Amersham).

mRNA reverse transcription reaction carried out in the presence of the oligo (dT) primer and the Superscript II enzyme (Gibco).

Resulting cDNA quantified using Nanovue (Amersham) and cDNAs adjusted to 10 ng/µl.

c) Quantitative PCR

The PCR reactions (polymerase chain reactions) were carried out by quantitative PCR with the "Light Cycler" system (Roche Molecular Systems Inc.) This analytical system makes it possible to carry out rapid and effective PCR reactions, in exchange for prior setting up of the analytical conditions for the various primers. It is made up of two main components:

an optimized thermocycler: allowing extremely rapid heat transfers;

a fluorimeter: allowing continuous measurement of the intensity of fluorescence incorporated into the DNA (detection at 521 nm).

Pairs of probes specific for the genes studied were used, allowing amplification of the following specific fragments:

| Gene name (protein encoded) | Abbreviation | Gene Bank | cDNA bp |
|---|---|---|---|
| Liver glyceraldehyde 3-phosphate | G3PDH | NM 002046 | 269 |
| Cytokeratin 6B | K6B | NM 005555 | 277 |
| Cytokeratin 10 | K10 | NM 000421 | 236 |
| Involucrin | INV | NM 005547 | 251 |

The reaction mixture (10 µl final) for each sample is the following:

2.5 µg of cDNA.

Primers for the various markers used.

Reaction mixture (Roche) containing the taq DNA polymerase enzyme, the SR Green I label (fluorophore which intercalates into double-stranded DNA during the elongation step) and $MgCl_2$.

d) Processing of Quantitative PCR Data

The incorporation of fluorescence into the amplified DNA is measured continuously during the PCR cycles. This system makes it possible to obtain curves of the fluorescence measurement as a function of the PCR cycles and thus to evaluate a relative expression value for each marker.

The number of cycles is determined on the basis of the "exit" points of the fluorescence curves. For a single marker analysed, the later a sample exits (high number of cycles), the lower the initial number of copies of the mRNA.

The relative expression value is expressed in arbitrary units according to the following formula:

$$(\tfrac{1}{2}^{\text{number of cycles}}) \times 10^6$$

e) Standardization of the Effects Observed on the Gene Expression

For a standardized interpretation, the following classification table was retained:

| % relative expression compared with the control | Classification of the effect observed |
|---|---|
| >150% and <200% | Moderate stimulation, to be confirmed |
| >200% | Clear stimulation |
| >300% | Strong stimulation |
| <65% and >50% | Moderate inhibition |
| <50% and >30% | Clear inhibition |
| <30% | Strong inhibition |

2—Results

The expression kinetics of the three studies relating to the markers are shown in Table 1 hereinafter and illustrated in FIG. 1.

The results are related to the amount of G3PDH messenger (reference gene) and expressed as % of the untreated control.

| | Treatment | K6B | K10 | INV |
|---|---|---|---|---|
| 6 hours | Control | 100 | 100 | 100 |
| | Composition A | 117 | 121 | 176 |
| | Composition B (lysate) | 176 | 102 | 153 |
| | Composition C (phytosphingosine) | 158 | 122 | 146 |
| | Composition D (combination) | 207 | 147 | 265 |

Under the experimental conditions of this test, it appears that only the combination in accordance with the invention increases, after 6 hours, the expression of the genes encoding cytokeratin 6B, cytokeratin 10 and involucrin.

Example 2

The compounds are, depending on the case, cited as chemical names or as CTFA (International Cosmetic Ingredient Dictionary and Handbook) names.

Face Care Composition in the Form of an Aqueous Gel

| | % by weight |
|---|---|
| Phytosphingosine-SLC ® | 0.002% |
| Repair Complex CLR ® | 10% |
| Sodium hyaluronate | 0.4% |
| Xanthan gum | 0.1% |
| 1,2-octanediol | 0.3% |
| Ethylenediaminetetraacetic acid, disodium salt | 0.099% |
| Glycerol | 5% |
| Citric acid | 0.015% |
| Ethyl alcohol | 4.6% |
| 4-(2-hydroxyethyl)piperazin-1-ethanesulphonic acid | 1% |
| Fatty substances | 0.016% |
| Emulsifier | 0.099% |
| Filler | 0.2% |
| Preservatives | 0.55% |
| Solvant | 1% |
| Fragrance | 0.005% |
| Water | QS 100% |

The above written description of the invention provides a manner and process of making and using it such that any person skilled in this art is enabled to make and use the same, this enablement being provided in particular for the subject matter of the appended claims, which make up a part of the original description. In the description herein, where a composition is described, a combination is included, and vice versa.

As used herein, the phrases "selected from the group consisting of," "chosen from," and the like include mixtures of the specified materials. Terms such as "contain(s)" and the like as used herein are open terms meaning 'including at least' unless otherwise specifically noted. The term "mentioned" notes exemplary embodiments, and is not limiting to certain species. As used herein the words "a" and "an" and the like carry the meaning of "one or more."

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention compositions and combinations are preferably used by human subjects desirous of the benefits noted herein, subjects "in need of" these benefits. Such subjects are typically suffering from one or more of the conditions, symptoms, etc. addressed by the present invention, such as by self diagnosis or cosmetician or medical diagnosis, or are at recognized and appreciated risk of developing such conditions, etc. and who intentionally use the invention methods, compositions and combinations to treat, address, combat, prevent, etc. the effects of such conditions, etc. The application also clearly describes and supports the simple application of the invention composition on the skin and its integuments regardless of any purpose or intent.

The invention claimed is:

1. A composition comprising, in a physiologically acceptable medium, at least one phytosphingosine salicylate derivative and at least one lysate of at least one microorganism of the genus *Bifidobacterium*, wherein said at least one phytosphingosine salicylate derivative is at least one compound of the formula:

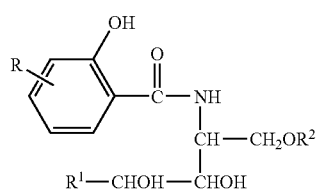

(I)

in which:
R represents:
a hydrogen atom,
a saturated or unsaturated, linear or branched $C_1$ to $C_{49}$ aliphatic radical, optionally substituted with a hydroxyl radical, or
a group $Y-O(C_aH_b)_m-$,
with a being an integer from 7 to 50, b an integer from 10 to 100, m is 0 or 1 and Y represents H or a $C_{14}$-$C_{22}$ fatty acid having the formula: $-CO-(C_xH_yZ_z)CH_3$,
with Z being $-OH$ or an epoxy oxygen, x an integer from 12 to 20, y an integer from 20 to 40, and z is 0 or an integer from 1 to 4;
$R^1$ represents a saturated or unsaturated, linear or branched $C_8$ to $C_{28}$ aliphatic radical, optionally substituted with a hydroxyl radical, and
$R^2$ represents H, a phosphate radical, a sulphate radical or a sugar,
wherein the at least one microorganism of the genus *Bifidobacterium* comprises *Bifidobacterium longum*, and
wherein the phytosphingosine salicylate derivative is present in a proportion of at least 0.0001% expressed as dry weight, relative to the total weight of the composition.

2. The composition according to claim 1, wherein R and $R^2$ are, respectively, a hydrogen atom and $R^1$ is a saturated, linear alkyl radical.

3. The composition according to claim 1, comprising a phytosphingosine salicylate derivative of the formula:

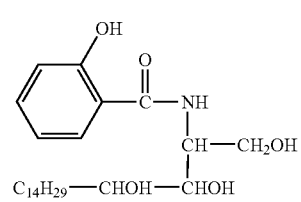

(V)

a salt thereof, or both.

4. The composition according to claim 1, wherein said composition is suitable for topical administration.

5. The composition according to claim 4, wherein the said composition is in the form of an aqueous solution, an aqueous-alcoholic solution, an oily solution, a dispersion in the form of a lotion, a dispersion in the form of a serum, a liquid emulsion in the form of a milk, a semi-liquid emulsion in the form of a milk, an O/W emulsion having liquid consistency, an O/W emulsion having semi-liquid consistency, a W/O emulsion having liquid consistency, a W/O emulsion having semi-liquid consistency, a suspension in the form of a cream having semi-solid or solid consistency, an emulsion in the form of a cream having semi-solid or solid consistency, an aqueous gel, an anhydrous gel, a microemulsion, microcapsules, microparticles, or ionic and/or nonionic vesicular dispersion.

6. A method for stimulating the expression of at least one gene selected from the group consisting of KRTB6, KRT10 and involucrin, comprising applying the composition of claim 1 to the skin of an individual in need thereof.

7. A method of treating skin aging in a subject comprising administering the composition of claim 1 to the subject.

8. A method for reinforcing the repair and regeneration capacity of an epithelium comprising applying the composition of claim 1 to the skin of an individual in need thereof.

* * * * *